United States Patent [19]

Elbe et al.

[11] Patent Number: 5,712,304
[45] Date of Patent: Jan. 27, 1998

[54] CARBOXYLIC ACID AMIDE BENZOTHIOPHENECARBOXAMIDE S-OXIDES

[75] Inventors: Hans-Ludwig Elbe; Reinhard Lantzsch, both of Wuppertal; Ralf Tiemann, Leverkusen; Heinz-Wilhelm Dehne, Bonn; Martin Kugler, Leichlingen; Wilfried Paulus; Heinrich Schrage, both of Krefeld, all of Germany

[73] Assignee: Bayer Aktiengesellschaft, Leverkusen, Germany

[21] Appl. No.: 553,593

[22] PCT Filed: May 9, 1994

[86] PCT No.: PCT/EP94/01488

§ 371 Date: Nov. 14, 1995

§ 102(e) Date: Nov. 14, 1995

[87] PCT Pub. No.: WO94/27986

PCT Pub. Date: Dec. 8, 1994

[30] Foreign Application Priority Data

May 21, 1993 [DE] Germany .......... 43 17 076.5

[51] Int. Cl.$^6$ .......... A01N 43/12; C07D 333/70
[52] U.S. Cl. .......... 514/272.4; 549/53
[58] Field of Search .......... 549/53; 514/443

[56] References Cited

U.S. PATENT DOCUMENTS

| | | | |
|---|---|---|---|
| 3,636,050 | 1/1972 | Driscoll et al. | 549/53 |
| 5,244,893 | 9/1993 | Elbe et al. | 514/212 |
| 5,342,835 | 8/1994 | Pepin et al. | 514/227.5 |
| 5,356,926 | 10/1994 | Boschelli et al. | 514/445 |

FOREIGN PATENT DOCUMENTS 146243  6/1985  European Pat. Off. .

*Primary Examiner*—Patricia L. Morris
*Attorney, Agent, or Firm*—Sprung Kramer Schaefer & Briscoe

[57] ABSTRACT

New benzothiophenecarboxamide S-oxides of the formula (I)

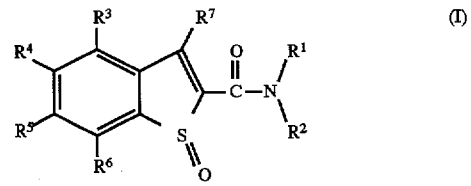

in which $R^1$ represents optionally substituted alkyl, or represents alkenyl or alkinyl, or represents in each case optionally substituted cycloalkyl or cycloalkylalkyl, or represents in each case optionally substituted aralkyl, aralkenyl, aralkinyl or aryl and $R^2$ represents hydrogen or optionally substituted alkyl, or $R^1$ and $R^2$ together with the nitrogen atom to which they are bonded represent an optionally substituted heterocycle, $R^3$, $R^4$, $R^5$ and $R^6$ independently of one another in each case represent hydrogen, halogen, cyano, nitro, alkyl, alkoxy, alkylthio, halogenoalkyl, halogenoalkoxy or halogenoalkylthio, and $R^1$ represents hydrogen or halogen, a process for their preparation, and their use as microbicides in plant protection and in the protection of materials.

New intermediates for the preparation of substances of the formula (I).

4 Claims, No Drawings

CARBOXYLIC ACID AMIDE BENZOTHIOPHENECARBOXAMIDE S-OXIDES

The invention relates to new benzothiophenecarboxamide S-oxides, to a process for their preparation, and to their use as microbicides in plant protection and in the protection of materials.

It has been disclosed that certain benzothiophenecarboxamide S,S-dioxides, such as, for example, the compound N-(methyl)-benzothiophene-2-carboxamide S,S-dioxide, have fungicidal properties (cf., for example, DE-OS (German Published Specification) 4,115,184).

However, the effectiveness of these prior-art compounds is not entirely satisfactory in all fields of application, in particular when low amounts and concentrations are applied.

New benzothiophenecarboxamide S-oxides of the formula (I)

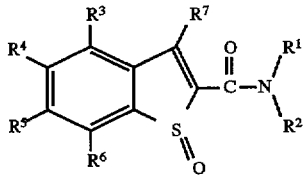

have been found in which

R¹ represents optionally substituted alkyl, or represents alkenyl or alkinyl, or represents in each case optionally substituted cycloalkyl or cycloalkylalkyl, or represents in each case optionally substituted aralkyl, aralkenyl, aralkinyl or aryl and R² represents hydrogen or optionally substituted alkyl, or R¹ and R2 together with the nitrogen atom to which they are bonded represent an optionally substituted heterocycle, R³, R⁴, R⁵ and R⁶ independently of one another in each case represent hydrogen, halogen, cyano, nitro, alkyl, alkoxy, alkylthio, halogenoalkyl, halogenoalkoxy or halogenoalkylthio, and R⁷ represents hydrogen or halogen.

If appropriate, the compounds of the formula (I) can exist in the form of geometric and/or optical isomers or variously composed mixtures of isomers, depending on the nature of the substituents. The pure isomers and also the isomer mixtures are claimed according to the invention.

Furthermore, it has been found that the new substituted thiophenecarboxamides of the formula (I)

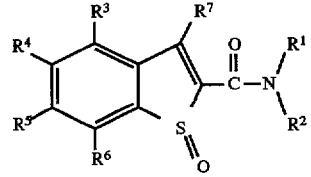

in which

R¹ represents optionally substituted alkyl, or represents alkenyl or alkinyl, or represents in each case optionally substituted cycloalkyl or cycloalkylalkyl, or represents in each case optionally substituted aralkyl, aralkenyl, aralkinyl or aryl and R² represents hydrogen or optionally substituted alkyl, or R¹ and R² together with the nitrogen atom to which they are bonded represent an optionally substituted heterocycle, R³, R⁴, R⁵ and R⁶ independently of one another in each case represent hydrogen, halogen, cyano, nitro, alkyl, alkoxy, alkylthio, halogenoalkyl, halogenoalkoxy or halogenoalkylthio, and R⁷ represents hydrogen or halogen, are obtained when benzothiophenecarboxamides of the formula (II)

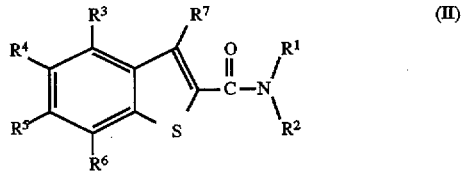

in which

R¹, R², R³, R⁴, R⁵, R⁶ and R⁷ have the abovementioned meaning are reacted with an oxidant, if appropriate in the presence of a diluent and if appropriate in the presence of a catalyst.

Finally, it has been found that the novel benzothiophenecarboxamide S-oxides of the formula (I) have powerful microbicidal properties and can be employed both in plant protection and in the protection of materials.

Surprisingly, the benzothiophenecarboxamide S-oxides of the formula (I) according to the invention display a considerably better effectiveness against plant-pathogenic microorganisms than, for example, the compound N-(methyl)-benzothiophene-2-carboxamide S,S-dioxide, which is a prior-art active compound having the same direction of action and similar constitution.

Formula (I) provides a general definition of the benzothiophenecarboxamide S-oxides according to the invention.

R¹ preferably represents straight-chain or branched alkyl having 1 to 20 carbon atoms which is optionally substituted by a nitrogen-bonded, saturated heterocycle which has 1 nitrogen atom and 2 to 6 carbon atoms and which can additionally be substituted by halogen, in each case straight-chain or branched alkyl or alkoxy, each of which has 1 to 4 carbon atoms, or straight-chain or branched halogenoalkyl having 1 to 4 carbon atoms and 1 to 9 identical or different halogen atoms, or represents in each case straight-chain or branched halogenoalkyl, cyanoalkyl, hydroxyalkyl, alkoxyalkyl or alkoxycarbonylalkyl, each of which has 1 to 8 carbon atoms in the individual alkyl moieties, or represents straight-chain or branched alkenyl having 2 to 12 carbon atoms, or represents straight-chain or branched alkinyl having 2 to 12 carbon atoms, or represents cycloalkylalkyl or cycoakyl, each of which has 3 to 7 carbon atoms in the cycloalkyl moiety and, if appropriate, 1 to 6 carbon atoms in the straight-chain or branched alkyl moiety and each of which is optionally mono- to hexa-substituted in the cycloalkyl moiety by identical or different substituents, suitable cycloalkyl substituents in each case being:

halogen, in each case straight-chain or branched alkyl having 1 to 4 carbon atoms or in each case straight-chain or branched halogenoalkyl having 1 to 4 carbon atoms and 1 to 9 identical or different halogen atoms; furthermore represents arylalkyl, arylalkenyl, arylalkinyl or aryl, each of which has 6 or 10 carbon atoms in the aryl moiety and, if appropriate, up to 12 carbon atoms in the in each case straight-chain or branched alkyl, alkenyl or alkinyl moiety and each of which is optionally mono- to pentasubstituted in the aryl moiety by identical or different substituents, suitable aryl substituents in each case being:

halogen, hydroxyl, cyano, nitro, formylamido, in each case straight-chain or branched alkyl, alkoxy or alkylthio, each of which has 1 to 4 carbon atoms, cycloalkyl having 3 to 7 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkylcarbonyl, alkoxycarbonyl, aminocarbonyl, N-alkylaminocarbonyl, N,N-dialkylaminocarbonyl, alkylcarbonylamino, N-alkyl-alkylcarbonylamino, N-alkyl-formylcarbonylamino or alkoximinoalkyl, each of which has 1 to 4 carbon atoms in the individual alkyl moieties, and phenyl which is optionally mono-substituted or polysubstituted by identical or different substituents from the series consisting of halogen and straight-chain or branched alkyl having 1 to 4 carbon atoms.

$R^2$ preferably represents hydrogen, or represents straight-chain or branched alkyl having 1 to 6 carbon atoms which is optionally monosubstituted or polysubstituted by identical or different substituents, suitable substituents in each case being:

hydroxyl, halogen, cyano, and in each case straight-chain or branched alkoxy, alkoxycarbonyl or dialkylamino, each of which has 1 to 6 carbon atoms in the individual alkyl moieties, or $R^1$ and $R^2$ preferably together with the nitrogen atom to which they are bonded represent a saturated five- to seven-membered heterocycle which can optionally contain one or two further hetero atoms—in particular nitrogen, oxygen and/or sulphur—and which is optionally monosubstituted or polysubstituted by identical or different substituents, suitable substituents in each case being:

halogen, in each case straight-chain or branched alkyl or alkoxy, each of which has 1 to 4 carbon atoms, or straight-chain or branched halogenoalkyl having 1 to 4 carbon atoms and 1 to 9 identical or different halogen atoms.

$R^3$, $R^4$, $R^5$ and $R^6$ preferably independently of one another in each case represent hydrogen, halogen, cyano, nitro, or represent in each case straight-chain or branched alkyl, alkoxy, alkylthio, halogenoalkyl, halogenoalkoxy or halogenoalkylthio, each of which has 1 to 6 carbon atoms and, if appropriate, 1 to 13 identical or different halogen atoms.

$R^7$ preferably represents hydrogen, fluorine, chlorine or bromine.

$R^1$ particularly preferably represents straight-chain or branched alkyl having 1 to 18 carbon atoms which is optionally substituted by a nitrogen-bonded, saturated heterocycle which has I nitrogen atom and 2 to 6 carbon atoms and which can additionally be substituted by halogen, in each case straight-chain or branched alkyl or alkoxy, each of which has 1 to 4 carbon atoms, or straight-chain or branched halogenoalkyl having 1 to 4 carbon atoms and 1 to 9 identical or different halogen atoms, or represents in each case straight-chain or branched halogenoalkyl, cyanoalkyl, hydroxyalkyl, alkoxyalkyl or alkoxycarbonylalkyl, each of which has 1 to 4 carbon atoms in the individual alkyl moieties, or represents straight-chain or branched alkenyl having 2 to 8 carbon atoms, or represents straight-chain or branched alkinyl having 2 to 8 carbon atoms, or represents cycloalkylalkyl or cycloalkyl, each of which has 3 to 6 carbon atoms in the cycloalkyl moiety, and, if appropriate, 1 to 4 carbon atoms in the straight-chain or branched alkyl moiety and each of which is optionally mono- to tetrasubstituted in the cycloalkyl moiety by identical or different substituents, suitable cycloalkyl substituents in each case being:

fluorine, chlorine, bromine, methyl, ethyl, n- or i-propyl, n-, i-, s- or t-butyl, chloromethyl, dichloromethyl or trifluoromethyl; furthermore represents arylalkyl, arylalkenyl, arylalkinyl or aryl, each of which has 6 or 10 carbon atoms in the aryl moiety and, if appropriate, up to 8 carbon atoms in the in each case straight-chain or branched alkyl, alkenyl or alkinyl moiety and each of which is optionally mono- to pentasubstituted in the aryl moiety by identical or different substituents, suitable aryl substituents in each case being:

halogen, hydroxyl, cyano, nitro, formylamido, in each case straight-chain or branched alkyl, alkoxy or alkylthio, each of which has 1 to 4 carbon atoms, cycloalkyl having 3 to 7 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkylcarbonyl, alkoxycarbonyl, aminocarbonyl, N-alkylaminocarbonyl, N,N-dialkylaminocarbonyl, alkylcarbonylamino, N-alkyl-alkylcarbonylamino, N-alkyl-formylcarbonylamino or alkoximinoalkyl, each of which has 1 to 4 carbon atoms in the individual alkyl moieties, and phenyl which is optionally monosubstituted to trisubstituted by identical or different substituents from the series consisting of halogen and straight-chain or branched alkyl having 1 to 4 carbon atoms.

$R^2$ particularly preferably represents hydrogen or represents straight-chain or branched alkyl having 1 to 4 carbon atoms which is optionally monosubstituted or polysubstituted by identical or different substituents, suitable substituents being:

hydroxyl, halogen, cyano, and in each case straight-chain or branched alkoxy, alkoxycarbonyl or dialkylamino, each of which has 1 to 4 carbon atoms in the individual alkyl moieties, or $R^1$ and $R^2$ particularly preferably together with the nitrogen atom to which they are bonded represent a heterocycle of the formula

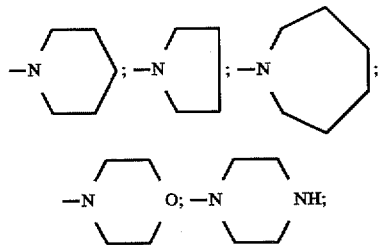

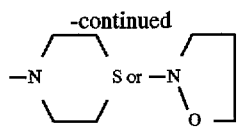

which is optionally monosubstituted to tetrasubstituted by identical or different substituents, suitable substituents in each case being: fluorine, chlorine, bromine, methyl, ethyl, n- or i-propyl, methoxy, ethoxy, chloromethyl, trichloromethyl, dichloromethyl, trifluoromethyl or difluoromethyl.

$R^3$, $R^4$, $R^5$ and $R^6$ particularly preferably independently of one another in each case represent hydrogen, halogen, cyano, nitro, or represent in each case straight-chain or branched alkyl, alkoxy, alkylthio, halogenoalkyl, halogenoalkoxy or halogenoalkylthio, each of which has 1 to 4 carbon atoms and, if appropriate, 1 to 9 identical or different halogen atoms.

$R^7$ particularly preferably represents hydrogen, chlorine or bromine.

$R^1$ very particularly preferably represents methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl, n- or i-dodecyl, n- or i-octadecyl, or represents allyl, n- or i-butenyl, n- or i-pentenyl, n- or i-hexenyl, propargyl, n- or i-butinyl, n- or i-pentinyl, n- or i-hexinyl, chloromethyl, bromomethyl, chloroethyl, bromoethyl, chloropropyl, bromopropyl, cyanomethyl, cyanoethyl, cyanopropyl, hydroxymethyl, hydroxyethyl, hydroxypropyl, methoxymethyl, methoxyethyl, methoxypropyl, ethoxymethyl, ethoxyethyl, ethoxypropyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl; furthermore represents cyclopropyl, cyclopropylmethyl, cyclopropylethyl, cyclopropylpropyl, cyclopentyl, cyclopentylmethyl, cyclopentylethyl, cyclopentylpropyl, cyclohexyl, cyclohexylmethyl, cyclohexylethyl or cyclohexylpropyl, each of which is optionally mono- to tetrasubstituted in the cycloalkyl moiety by identical or different substituents from the series consisting of fluorine, chlorine, bromine, methyl, ethyl, n- or i-propyl, chloromethyl, dichloromethyl or trifluoromethyl; furthermore represents phenylalkyl, phenylalkenyl, phenylalkinyl, phenyl or naphthyl, each of which has, if appropriate, up to 6 carbon atoms in the straight-chain or branched alkyl, alkenyl or alkinyl moiety and each of which is optionally mono- to trisubstituted in the aryl moiety by identical or different substituents, suitable aryl substituents in each case being:

fluorine, chlorine, bromine, hydroxyl, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, cyclopropyl, cyclopentyl, cyclohexyl, cycloheptyl, trifluoromethyl, trifluoromethoxy, trifluoromethylthio, methylcarbonyl, ethylcarbonyl, methoxycarbonyl, ethoxycarbonyl, aminocarbonyl, N-methylamino-carbonyl, N,N-dimethylaminocarbonyl, N-ethylaminocarbonyl N,N-diethylaminocarbonyl, N-formylamino, N-acetylamino, N-methyl-N-formylamino, N-methyl-N-acetylamino, N-ethyl-N-formylamino, N-ethyl-N-acetylamino, methoximinomethyl, methoximinoethyl, ethoximinomethyl, ethoximinoethyl or phenyl which is optionally mono- to trisubstituted by identical or different substituents from the series consisting of fluorine, chlorine, bromine, methyl and ethyl.

$R^2$ very particularly preferably represents hydrogen, methyl, ethyl, n- or i-propyl, n-, i-, s- or t-butyl, n- or i-pentyl, n- or i-hexyl, hydroxymethyl, hydroxyethyl, hydroxypropyl, chloromethyl, bromomethyl, chloroethyl, bromoethyl, chloropropyl, bromopropyl, cyanomethyl, cyanoethyl, cyanopropyl, methoxymethyl, methoxyethyl, methoxypropyl, ethoxymethyl, ethoxyethyl, ethoxypropyl, methoxycarbonylmethyl, methoxycarbonylethyl, methoxycarbonylpropyl, ethoxycarbonylmethyl, ethoxycarbonylethyl, ethoxycarbonylpropyl, propoxycarbonylmethyl, propoxycarbonylethyl, propoxycarbonylpropyl, dimethylaminomethyl, diethylaminomethyl, dipropylaminomethyl, dimethylaminoethyl, diethylaminoethyl, dipropylaminoethyl, dimethylaminopropyl, diethylaminopropyl or dipropylaminopropyl or $R^1$ and $R^2$ very particularly preferably together with the nitrogen atom to which they are bonded represent a heterocycle of the formula

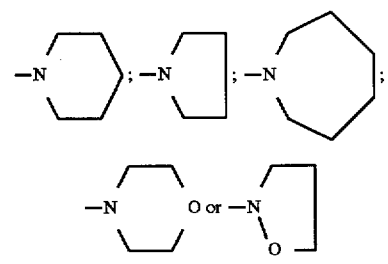

which is optionally monosubstituted to trisubstituted by identical or different substituents from the series consisting of methyl and ethyl.

$R^3$, $R^4$, $R^5$ and $R^6$ very particularly preferably independently of one another in each case represent hydrogen, fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy, trifluoromethylthio.

$R^7$ very particularly preferably represents hydrogen or chlorine.

If, for example, N-(3-chlorophenyl)-benzothiophene-2-carboxamide is used as starting compound and m-chloroperbenzoic acid as the oxidant, the course of the reaction of the process according to the invention can be represented by the following equation:

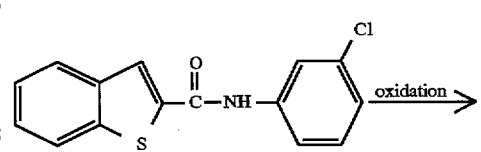

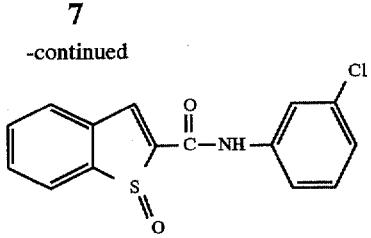

Formula (II) provides a definition of the benzothiophenecarboxamides required as starting substances for carrying out the process according to the invention. In this formula (II), $R^1$, $R^2$, $R^{3,}$ $R^{4,}$ $R^5$, $R^6$ and $R^7$ preferably represent those radicals which have already been mentioned in connection with the description of the compounds of the formula (I) according to the invention as being preferred for these substituents. The benzothiophenecarboxamides of the formula (II) are known or can be obtained in analogy to known processes (cf., for example, DE 3 832 846; DE 3 832 848; EP 374 048; EP 253 650; Ind. J. Chem. Sect. B, 23B, 38–41 [1984]; Tetrahedron 34, 3545–3551 [1978]; Collect. Czech. Chem. Commun. 51, 2002–2012 [1986]; J. Org. Chem. 40, 3037–3045 [1975]; Liebigs Ann. Chem. 760, 37–87 [1972] and the preparation examples).

Benzothiophenecarboxamides of the formula (IIa)

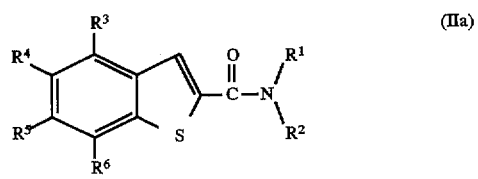

in which $R^1$, $R^2$, $R^3$, $R^4$, $R^5$ and $R^6$ have the abovementioned meaning are alternatively also obtained by a new process which is also provided by the invention, by reacting benzothiophenecarboxamides of the formula (IIb)

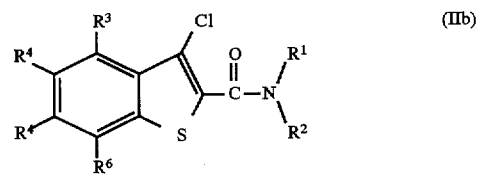

in which $R^1$, $R^2$, $R^3$, $R^4$, $R^5$ and $R^6$ have the abovementioned meaning with molecular hydrogen in the presence of a diluent and in the presence of a catalyst and, if appropriate, in the presence of a base.

It must be considered as surprising and unforeseeable by the expert that this reductive dehalogenation reaction with catalytically activated hydrogen does not simultaneously result in hydrogenation of the double bond in the benzothiophene moiety of the molecule.

A particular advantage of this process for synthesizing the benzothiophenecarboxamides of the formula (IIa) which are used as precursors is the fact that, as opposed to the prior-art processes (of., for example, DE 4 115 184), the starting material used in the present case, the starting materials are particularly readily accessible and inexpensive cinnamic acid derivatives whose reaction with thionyl chloride yields the benzothiophenecarboxamides of the formula (IIb) required in a smooth reaction (cf., for example, DE 3 832 846; DE 3 832 848).

Suitable diluents for carrying out this dehalogenation process according to the invention are all customary inorganic solvents. These include, in particular, aliphatic, alicyclic or aromatic hydrocarbons such as, for example, benzene, benzene, toluene, xylene, petroleum ether, hexane, cyclohexane; ethers, such as diethyl ether, diisopropyl ether, methyl tert-butyl ether, methyl tert-amyl ether, dioxane, tetrahydrofuran, ethylene glycol dimethyl ether or ethylene glycol diethyl ether; diethylene glycol dimethyl ether or diethylene glycol diethyl ether, or anisole; amides, such as formamide, N,N-dimethylformamide, N,N-dibutylformamide, N,N-dimethylacetamide, N-methylformanilide, N-methylpyrrolidone, N-methyl-ε-caprolactam or hexamethylphosphoric triamide; esters, such as methyl acetate, ethyl acetate or butyl acetate; alcohols, such as methanol, ethanol, n- or i-propanol, n-, i-, s- or t-butanol, ethylene glycol, ethylene glycol monomethyl ether or ethylene glycol monoethyl ether, their mixtures with water, or pure water. Polar diluents are particularly preferably used.

Suitable catalysts for carrying out this dehalogenation process according to the invention are customary reduction catalysts. Catalysts which are particularly preferably used are noble-metal catalysts, such as, for example, palladium or palladium salts, or else Raney catalysts, such as Raney nickel or Raney cobalt, if appropriate on a suitable support material, such as, for example, carbon or silicon dioxide.

The dehalogenation process according to the invention is preferably carried out in the presence of a base. Suitable bases are all customary inorganic or organic bases. These include, for example, the hydroxides, acetates, carbonates or hydrogen carbonates of alkaline earth metals, alkali metals or of ammonium, such as, for example, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines, such as trimethylamine, triethylamine, tributylamine, N,N-dimethylaniline, N,N-dimethylbenzylamine, N,N-dimethylcyclohexylamine, pyridine, N-methylpiperidine, N,N-dimethylaminopyridine, diazabicyclooctane (DABCO), diazabicyclononene (DBN) or diazabicycloundecene (DBU). If appropriate, it is also possible to use a suitable excess of base simultaneously as the diluent.

When carrying out the dehalogenating process according to the invention, the reaction temperatures can be varied within a substantial range. In general, the process is carded out at temperatures between 10° C. and 150° C., preferably at temperatures between 30° C. and 120° C.

The dehalogenation process according to the invention is customarily carded out under pressure. In general, the process is carded out in pressure ranges between 1 bar and 150 bar, preferably between 2 bar and 80 bar.

To carry out the dehalogenation process according to the invention, 0.0001 to 1.0 mol, preferably 0.001 to 0.1 mol, of hydrogenation catalyst and 1.0 to 5.0 mol, preferably 1.0 to 2.5 mol, of base are generally employed per mole of benzothiophenecarboxamide of the formula (IIb), and molecular hydrogen is then added at the temperature required until the pressure required is established. The reaction is carried out and the reaction products are worked up and isolated in a generally customary manner (cf. in this context also the preparation examples).

Suitable oxidants for carrying out the oxidation reaction according to the invention are all oxidants which can customarily be used for the oxidation of sulphur. Hydrogen peroxide or organic peracids, such as, for example, peracetic acid, 4-nitroperbenzoic acid or 3-chloroperbenzoic acid, are preferably used.

Depending on the oxidant used, suitable diluents for carrying out the oxidation process according to the invention are inorganic or organic solvents. The following are preferably used: alcohols, such as, for example, methanol or ethanol, or their mixtures with water or pure water; acids, such as, for example, acetic acid, acetic anhydride or propionic acid, or dipolar aprotic solvents, such as acetonitrile, acetone, ethyl acetate or dimethylformamide, and also optionally halogenated hydrocarbons, such as benzine, benzene, toluene, hexane, cyclohexane, petroleum ether, dichloromethane, dichloroethane, chloroform, carbon tetrachloride or chlorobenzene.

If appropriate, the oxidation process according to the invention can also be carried out in the presence of a suitable catalyst. Suitable catalysts which can be used are all those which can be used customarily for such sulphur oxidation reactions. Heavy metal catalysts are preferably used; an example which may be mentioned in this context is ammonium molybdate.

When carrying out the oxidation process according to the invention, the reaction temperatures can be varied within a substantial range. In general, the process is carried out at temperatures between −30° C. and +50° C., preferably at temperatures between 0° C. and +25° C.

To carry out the oxidation process according to the invention, 2.0 to 10.0 mol, preferably 1.0 to 2.5 mol, of oxidant and, if appropriate, 0.001 to 1.0 mol, preferably 0.005 to 0.05 mol, of catalyst are generally employed per mole of benzothiophene- carboxamide of the formula (II).

The reaction is carried out and the reaction products are worked up and isolated by customary, known processes (cf. in this context the preparation examples).

The end products of the formula (I) are purified with the aid of customary processes, for example by column chromatography or by recrystallization. They are characterized with the aid of the melting point or, in the case of compounds which do not crystallize, with the aid of the refractive index or proton nuclear resonance spectroscopy ($^1$H NMR).

The active compounds according to the invention have a powerful microbicidal activity and can be employed as fungicides in plant protection and in the protection of materials.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal diseases which come under the generic names listed above may be mentioned as examples, but not by way of limitation:

Pythium species, such as, for example, *Pythium ultimum*;
Phytophthora species, such as, for example, *Phytophthora infestans*;
Pseudoperonospora species, such as, for example, *Pseudoperonospora humuli* or *Pseudoperonospora cubensis*;
Plasmopara species, such as, for example, *Plasmopara viticola*;
Peronospora species, such as, for example, *Peronospora pisi* or *Peronospora brassicae*;
Erysiphe species, such as, for example, *Erysiphe graminis*;
Sphaerotheca species, such as, for example, *Sphaerotheca fuliginea*;
Podosphaera species, such as, for example, *Podosphaera leucotricha*;
Venturia species, such as, for example, *Venturia inaequalis*;
Pyrenophora species, such as, for example, *Pyrenophora teres* or *Pyrenophora graminea* (conidia form: Drechslera, synonym: Helminthosporium);
Cochliobolus species, such as, for example, *Cochliobolus sativus* (conidia form: Drechslera, synonym: Helminthosporium);
Uromyces species, such as, for example, *Uromyces appendiculatus*;
Puccinia species, such as, for example, *Puccinia recondita*;
Tilletia species, such as, for example, *Tilletia caries*;
Ustilago species, such as, for example, *Ustilago nuda* or *Ustilago avenae*;
Pellicularia species, such as, for example, *Pellicularia sasakii*;
Pyricularia species, such as, for example, *Pyricularia oryzae*;
Fusarium species, such as, for example, *Fusarium culmorum*;
Botrytis species, such as, for example, *Botrytis cinerea*;
Septoria species, such as, for example, *Septoria nodorum*;
Leptosphaeria species, such as, for example, *Leptosphaeria nodorum*;
Cercospora species, such as, for example, *Cercospora canescens*;
Alternaria species, such as, for example, *Alternaria brassicae* and
Pseudocercosporella species, such as, for example, *Pseudocercosporella herpotrichoides*.

The good toleration, by plants, of the active compounds, at the concentrations required for combating plant diseases, permits treatment of above-ground parts of plants, of vegetative propagation stock and seeds, and of the soil.

The active compounds according to the invention can be employed particularly successfully for combating diseases in fruit and vegetable growing, such as, for example, against the causative organism of tomato blight (*Phytophthora infestans*) or for combating cereal diseases, such as, for example, against the causative organism of net blotch of barley (*Pyrenophora teres*) or against the causative organism of leaf spot of barley or wheat (*Cochliobolus sativus*) or against the causative organism of glume blotch of wheat (*Septoria nodorum*) or for combating rice diseases, such as, for example, against the causative organism of rice blast disease (*Pyricularia oryzae*) or against the causative organism of rice stem blight (*Pellicularia sasakii*). In addition, the active compounds according to the invention also have a good in-vitro activity.

Moreover, the active compounds according to the invention can be employed for protecting industrial materials against infection with, and destruction by, undesired microorganisms.

Industrial materials in the present context are to be understood as meaning non-living materials which have been prepared for use in industry. For example, industrial materials which are intended to be protected by active compounds according to the invention from microbial change or destruction can be glues, sizes, papers and board, textiles, leather, wood, paints and plastic articles, cooling lubricants and other materials which can be infected with, or destroyed by, microorganisms. Parts of production plants, for example cooling-water circuits, which may be impaired by the multiplication of microorganisms may also be mentioned within the scope of the materials to be protected. Industrial materials which may be mentioned within the scope of the present invention are preferably glues, sizes, papers and boards, leather, wood, paints, cooling lubricants and heat-transfer liquids, particularly preferably wood.

The compounds according to the invention are preferably suitable for the protection of paints against infection with, and destruction by, microorganisms.

Microorganisms which are capable of bringing about degradation of, or change in, the industrial materials are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae.

Microorganisms of the following genera may be mentioned as examples:

Alternaria, such as *Alternaria tenuis*;
Aspergillus, such as *Aspergillus niger*;
Chaetomium, such as *Chaetominum globosum*;
Coniophora, such as *Coniophora puteana*;
Lentinus, such as *Lentinus tigrinus*;
Penicillium, such as *Penicillium glaucum*;
Polyporus, such as *Polyporus versilicolor*;
Aureobasidium, such as *Aureobasidium pullulans*;
Sclerophoma, such as *Sclerophoma pityophila*;
Trichoderma, such as *Trichoderma viride*;
Escherichia, such as *Escherichia coil*;
Pseudomonas, such as *Pseudomonas aeruginosa*;
Staphylococcus, such as *Staphylococcus aureus*.

Depending on their particular physical and/or chemical properties and on the field of application, the active compounds can be converted to the customary formulations, such as solutions, emulsions, suspensions, powders, foams, pastes, granules, aerosols, very fine capsules in polymeric substances and in coating compositions for seed, as well as ULV cold mist and warm mist formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents, such as for example, alcohols can also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes, such as 1,2-dichloroethane or methylene chloride, aliphatic hydrocarbons, such as cyclohexane or paraffins, for example benzine or other mineral oil fractions, alcohols, such as ethanol, isopropanol, butanol, benzyl alcohol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

When used in plant protection, the formulations in general comprise between 0.1 and 95 per cent by weight of active compound, preferably between 0.5 and 90%.

When used in plant protection, the active compounds according to the invention can exist, in the formulations, in the form of a mixture with other known active compounds, such as fungicides, insecticides, acaricides and herbicides, and in the form mixtures with fertilizers and growth regulators.

The active compounds can be used as such, in the form of their formulations or in the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low-volume method, or to inject the active compound preparation, or the active compound itself, into the soil. The seed of the plants can also be treated.

In the treatment of parts of plants, the active compound concentrations in the use forms can be varied within a substantial range they are generally between 1 and 0.0001% by weight, preferably between 0.5 and 0.001 % by weight.

In the treatment of seed, mounts of active compound of 0.001 to 50 g, preferably 0.01 to 10 g, are generally required per kilogram of seed.

In the treatment of the soil, active compound concentrations of 0.00001 to 0.1% by weight, preferably 0.0001 to 0.02 % by weight, are required at the site of action.

The compositions used for the protection of industrial materials generally comprise 10 1 to 95 %, preferably 10 to 75 %, of the active compounds.

The use concentrations of active compounds according to the invention depend on the species and the occurrence of the microorganisms to be combated and on the composition of the material to be protected. The optimum dosage rate can be determined by test series. In general, the use concentrations are in the range from 0.001 to 5 % by weight, preferably from 0.05 to 1.0 by weight, relative to the material to be protected.

The effectiveness and the spectrum of action of the active compounds which can be used according to the invention, or of the compositions, concentrates or quite generally formulations which can be prepared therefrom, can be increased by adding, if appropriate, other antimicrobially active compounds, fungicides, bactericides, herbicides, insecticides or other active compounds for broadening the spectrum of action or for achieving specific effects, such as, for example, the additional protection against insects. These mixtures may have a broader spectrum of action than the compounds according to the invention.

In many cases, synergistic effects are obtained, i.e. the effectiveness of the mixture exceeds the effectiveness of the individual components. Particularly components of mixtures are, for example, the following compounds:

Sulphenamides, such as dichlorfluanid (Euparen), tolyfluanid (Methyleuparen), folpet, fluorfolpet;

Benzimidazoles, such as carbendazim (MBC), benomyl, fuberidazole, thiabendazole or their salts;

Thiocyanates, such as thiocyanatomethylthiobenzothiazole (TCMTB), methylenebisthiocyanate (MBT);

Quaternary ammonium compounds, such as benzyldimethyltetradecylammonium chloride, benzyl-dimethyl-dodecyl-ammonium chloride, dodecyl-dimethyl-ammonium chloride;

Morpholine derivatives, such as $C_{11}$–$C_{14}$-4-alkyl-2,6-dimethyl-morpholine homologs (tridemorph), (±)-cis-4-[tert-butylphenyl)-2-methylpropyl]-2,6-dimethylmorpholine (fenpropimorph), falimorp;

Phenols, such as o-phenylphenol, tribromophenol, tetrachlorophenol, pentachlorophenol, 3-methyl-4-chlorophenol, dichlorophene, chlorophene, or their salts;

Azoles, such as triadimefon, triadimenol, bitertanol, tebuconazole, propiconazole, azaconazole, hexaconazole, prochloraz, cyproconazole, 1-(2-chlorocyclopropyl)-2-(1-chlorocyclopropyl)-3-(1,2,4-triazol-1-yl)-propan-2-ol or 1-(2-chlorophenyl)-2-(1,2,4-triazol-1-yl-methyl)-3,3-dimethyl-butan-2-ol;

Iodopropargyl derivatives, such as iodopropargyl butylcarbamate (IPBC), iodopropargylchlorophenyl formal, iodopropargyl phenylcarbamate, iodopropargyl hexylcarbamate, iodopropargyl cyclohexylcarbamate and iodopropargyl oxyethylphenylcarbamate;

Iodine derivatives such as diodomethyl-p-aryl sulphones, for example diiodomethyl-p-tolyl sulphone;

Bromine derivatives such as bromopol;

Isothiazolines such as N-methylisothiazolin-3-one, 5-chloro-N-methyliaothiazolin-3-one, 4,5-dichloro-N-octylisothiazolin-3-one, N-octylisothiazolin-3-on (octilinone);

Benzisothiazolinones, cyclopentene-isothiazolines;

Pyridines such as 1-hydroxy-2-pyridinethione (and their Na, Fe, Mn and Zn salts), tetrachloro-4-methylsulphonylpyridine;

Metal soaps, such as tin napthenate, tin octoate, tin 2-ethylhexanoate, tin oleate, tin phosphate, tin benzoate, copper napthenate, copper octoate, copper 2-ethylhexanoate, copper oleate, copper phosphate, copper benzoate, zinc napthenate, zinc octoate, zinc 2-ethylhexanoate, zinc oleate, zinc phosphate and zinc benzoate, and oxides such as TBTO, $Cu_2O$, CuO, ZnO;

Organotin compounds, such as tributyltin naphtenate and tributyltin oxide;

Dialkyldithiocarbamates, such as Na and Zn salts of dialkyldithiocarbamates, tetramethyltiuramidisulfide (TMTD);

Nitriles, such as 2,4,5,6-tetrachloroisophthalonitrile (chlorthalonil) and other microbicides having an activated halogen group, such as Cl—Ac, MCA, tectamer, bromopol, bromidox;

Benzothiazoles, such as 2-mercaptobenzothiazoles; s.a. dazomet;

Quinolines, such as 8-hydroxyquinoline;

Formaldehyde-releasing compounds, such as benzyl alcohol mono(poly)-hemiformal, oxazolidines, hexahydro-2-triazines, N-methylolchloroacetamide;

Tris-N-(cyclohexyldiazeniumdioxy)-aluminium, N-(cyclohexyldiazeniumdioxy)-tri-butyltin or K salts, bis-(N-oyclohexyl)diazinium -(dioxy-copper or aluminium).

Preferred insecticides which are added are:

Phosphoric esters, such as azinphos-ethyl, azinphos-methyl, 1-(4-chlorophenyl)-4-(O-ethyl, S-propyl) phosphoryloxypyrazole (TIA-230), chlorpyrifos, coumaphos, demeton, demeton-S-methyl, diazinon, dichlorfos, dimethoate, ethoprophos, etrimfos, fenitrothion, fention, heptenophos, parathion, parathion-methyl, phosalone, phoxim, pirimiphos-ethyl, pirimiphos-methyl, profenofos, prothiofos, sulprofos, triazophos and trichlorphon.

Carbamates such as aldicarb, bendiocarb, BPMC (2-(1-methylpropyl)phenyl methylcarbamate), butocarboxim, butoxycarboxim, carbaryl, carbofuran, carbosulfan, cloethocarb, isoprocarb, methomyl, oxamyl, pirimicarb, promecarb, propoxur and thiodicarb;

Pyrethroids, such as allethrin, alphamethrin, bioresmethrin, byfenthrin (FMC 54800), cycloprothrin, cyfluthrin, decamethrion, cyhalothrin, cypermethrin, deltamethrin, alpha-cyano-3-phenyl-2-methylbenzyl 2,2-dimethyl-3-(2-chloro-2-trifluoromethylvinyl)-cyclopropanecarboxylate, fenpropathrin, fenfluthrin, fenvalerate, flucythrinate, flumethrin, fluvalinate, permethrin and resmethrin, nitroimino and nitromethylene compounds such as 1-[(6-chloro-3-pyridinyl)-methyl-]-4,5-dihydro-N-nitro-1H-imidazol-2-amine (imidachloprid).

Organosilicon compounds, preferably dimethyl(phenyl) silylmethyl 3-phenoxybenzyl ethers, such as, for example, dimethyl-(4-ethoxyphenyl)-silylmethyl 3-phenoxybenzyl ether or dimethyl(phenyl)-silylmethyl 2-phenoxy-6-pyridylmethyl ethers, such as, for example, dimethyl(9-ethoxyphenyl)-silylmethyl 2-phenoxy6-pyridylmethyl ethers, or (phenyl)[3-(3-phenoxyphenyl)propyl](dimethyl)-silanes, such as, for example, (4-ethoxyphenyl)-[3(4-fluoro-3-phenoxyphenyl)-propyl]dimethylsilanes.

Other active compounds which are suitable are algicides, molluscicides and active compounds against sea animals which populate, for example, ships' bottom paints.

The preparation of active compounds and their use according to the invention are illustrated by the examples which follow.

PREPARATION EXAMPLES

Example 1

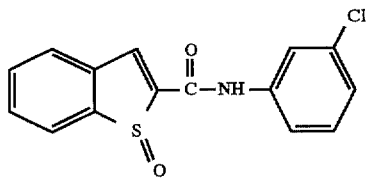

9.1 g (0.039 mol) of m-chloroperbenzoic acid (73 per cent strength) are added to 11.1 g (0.039 mol) of N-(3-chlorophenyl)-benzothiophene-2-carboxamide in 500 ml of dichloromethane at room temperature, with stirring, and the mixture is subsequently stirred at room temperature for 12 hours. For working-up, precipitated product is filtered off with suction, washed with dichloromethane and dried in vacuo at 50° C.

8.4 g (71% of theory) of N-(3-chlorophenyl)-benzothiophene-2-carboxamide-S-oxide of melting point 257°–258° C. are obtained.

Preparation of the starting compounds

Example II-1

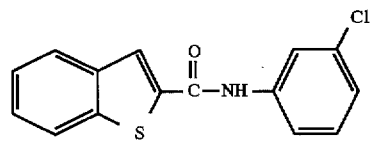

A solution of 3.2 g (0.025 mol) of 3-chloroaniline and 2.53 g of triethylamine in 30 ml of toluene is added to 5.0 g (0.025 mol) of benzothiophene-2-carboxylic acid chloride (CA Reg.No. 107943-19-1) in 60 ml of toluene at room temperature with cooling and stirring, and the mixture is subsequently stirred at 50° C. for 1 hour. For working-up, 60 ml of water are added, the precipitated product is filtered off with suction and washed with water, and the residue is dried in vacuo at 50° C.

7.0 g (97 % of theory) of N-(3-chlorophenyl)-benzothiophene-2-carboxamide of melting point 179° C. are obtained.

Example II-2

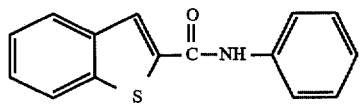

1.6 g of pulverized potassium hydroxide (88 per cent pure) and 1.0 g of palladium on active charcoal (10 per cent) are added to 7.2 g (0.025 mol) of 3-chloro-benzothiophene-2-carboxanilide in 25 ml of N-methylpyrrolidone at room temperature and the mixture is subsequently hydrogenated at 50° C. and a hydrogen pressure of 50 bar for 8 hours. For working-up, the catalyst is filtered off and washed twice using in each case 5 ml of N-methylpyrrolidone, the filtrate is concentrated in vacuo, the residue is treated with water, and the precipitated product is filtered off with suction, washed with water and dried.

5.5 g (86 % of theory) of benzothiophene-2-carboxanilide of melting point 188° C. are obtained.

The following benzothiophenecarboxamide S-oxides of the formula (I) are obtained in a corresponding manner and following the general preparation instructions:

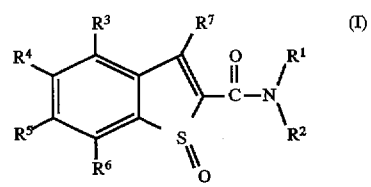

| Ex. No. | $-N\begin{smallmatrix}R^1\\R^2\end{smallmatrix}$ | $R^3, R^4, R^5, R^6$ | $R^7$ | Melting point/°C. |
|---|---|---|---|---|
| 2 | —NH—CH(CH₃)—C₆H₄—Cl | (benzo) | H | 65–69 (R form) |
| 3 | —NH—CH(CH₃)—C₆H₄—Cl | (benzo) | H | 68–71 |

-continued (I) Structure: phenyl ring with R³, R⁴, R⁵, R⁶ substituents, connected to C(R⁷)=C(S(=O))–C(=O)–N(R¹)(R²)

| Ex. No. | —N(R¹)(R²) | Aryl (R³,R⁴,R⁵,R⁶) | R⁷ | Melting point/°C. |
|---|---|---|---|---|
| 4 | —NH-n-C₄H₉ | C₆H₅ | H | 139–141 |
| 5 | —NH-(2,4,5-trimethylphenyl) | C₆H₅ | H | 194 |
| 6 | —NH—(CH₂)₃—N(aziridinyl) | C₆H₅ | H | oil |
| 7 | —NH-n-C₃H₇ | C₆H₅ | H | 158–160 |
| 8 | —NH—C₆H₅ | C₆H₅ | H | 228 |
| 9 | —NH-(2,4-dimethylphenyl) | C₆H₅ | H | >200 |
| 10 | —NH-(4-methylphenyl) | C₆H₅ | H | >200 |
| 11 | —NH-(4-chlorophenyl) | C₆H₅ | H | >200 |
| 12 | —N(CH₃)—C₆H₅ | C₆H₅ | H | 98 |
| 13 | —NH-(4-bromophenyl) | C₆H₅ | H | >200 |

-continued
   (I)
| Ex. No. | −N(R¹)(R²) | Ar (R³–R⁶) | R⁷ | Melting point/°C. |
|---|---|---|---|---|
| 14 | 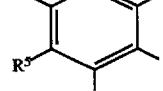 |  | H | >200 |
| 15 | —NH-i-C₄H₉ | 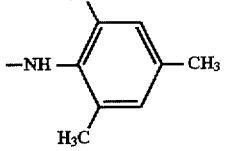 | H | 168–170 |
| 16 | —NH-t-C₄H₉ | 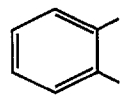 | H | 132–134 |
| 17 | 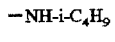 | 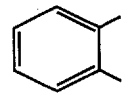 | H | >270 |
| 18 |  | 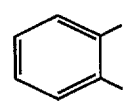 | H | 68 |
| 19 | 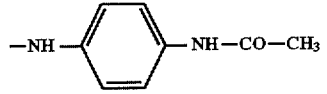 | 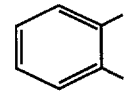 | H | 217–219 |
| 20 | 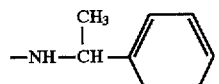 | 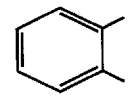 | H | 194–196 |
| 21 | —NH-n-C₁₂H₂₅ | 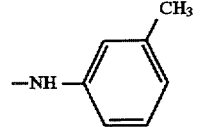 | H | 114–117 |
| 22 | —NH—C(CH₃)₂—C₂H₅ | 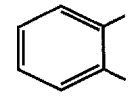 | H | 108–110 |
| 23 | 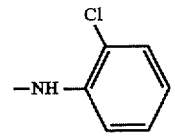 | 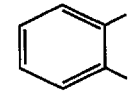 | H | 177–179 |

-continued

Structure (I): Phenyl ring with R³, R⁴, R⁵, R⁶ substituents; =C(R⁷)- connecting to a ring containing S=O, with C(=O)-N(R¹)(R²) group.

| Ex. No. | –N(R¹)(R²) | R³,R⁴,R⁵,R⁶ (phenyl) | R⁷ | Melting point/°C |
|---|---|---|---|---|
| 24 | –NH–(2-CH₃-C₆H₄) | C₆H₅ | H | 203–204 |
| 25 | –NH–(2,6-(CH₃)₂-C₆H₃) | C₆H₅ | H | 203–205 |
| 26 | –N(n-C₄H₉)–C₆H₅ | C₆H₅ | H | 130–132 |
| 27 | –NH–CH(CH₃)–(2-CH₃-C₆H₄) | C₆H₅ | H | 76 |
| 28 | –NH–(3,4-(CH₃)₂-C₆H₃) | C₆H₅ | H | 240–242 |
| 29 | –NH–(2,5-(CH₃)₂-C₆H₃) | C₆H₅ | H | 210–212 |
| 30 | –NH–(3,5-(CH₃)₂-C₆H₃) | C₆H₅ | H | 208–210 |
| 31 | –NH–(2,3-(CH₃)₂-C₆H₃) | C₆H₅ | H | 205–206 |

-continued

Structure (I): Benzene ring with substituents R³, R⁴, R⁵, R⁶ and R⁷ on vinyl connected to C(=O)-N(R¹)(R²), with S=O bridge.

| Ex. No. | -N(R¹)(R²) | R³,R⁴,R⁵,R⁶ (phenyl) | R⁷ | Melting point/°C. |
|---|---|---|---|---|
| 32 | $-NH-CH_2-C_6H_5$ | phenyl | H | 209–210 |
| 33 | $-N(C_2H_5)-C_6H_5$ | phenyl | H | 117–120 |
| 34 | $-NH-$(2,4-diCl-C₆H₃) | phenyl | H | 192–194 |
| 35 | $-NH-$(4-OCH₃-C₆H₄) | phenyl | H | 223–225 |
| 36 | $-NH-CH_2-$(4-Br-C₆H₄) | phenyl | H | 225–228 |
| 37 | $-NH-CH(CH_3)-$(4-OCH₃-C₆H₄) | phenyl | H | 65 |
| 38 | $-NH-CH_2-$(4-F-C₆H₄) | phenyl | H | 211 |
| 39 | $-NH-CH_2-$(4-Cl-C₆H₄) | phenyl | H | 217–219 |
| 40 | $-NH-i-C_4H_9$ | phenyl | Cl | 152–154 |
| 41 | $-NH-$cyclohexyl | phenyl | Cl | 214–216 |

-continued
| Ex. No. | -N(R¹)(R²) | Aryl (R³-R⁶) | R⁷ | Melting point/°C. |
|---|---|---|---|---|
| 42 | —NH—(2,5-dichlorophenyl) | phenyl | Cl | 225–227 |
| 43 | —NH—(2,3-dichlorophenyl) | phenyl | Cl | 199–200 |
| 44 | —NH—(4-OCF₃-phenyl) | phenyl | Cl | 190–192 |
| 45 | —NH—(CH₂)₂—C₆H₅ | phenyl | Cl | 152–153 |
| 46 | —N(CH₃)—CH₂—C₆H₅ | phenyl | Cl | 115–118 |
| 47 | —NH—(2-CH₃-5-Cl-phenyl) | phenyl | Cl | 220–222 |
| 48 | —NH—(2-CH₃-3-Cl-phenyl) | phenyl | Cl | 223–225 |
| 49 | —NH—(4-C₂H₅-phenyl) | phenyl | Cl | 160–162 |
| 50 | —NH—(2,6-di-i-C₃H₇-phenyl) | phenyl | Cl | 259–261 |

-continued

Structure (I): Aryl group with R³, R⁴, R⁵, R⁶ substituents connected to C=C(R⁷)–C(=O)–N(R¹)(R²), with S(=O) group.

| Ex. No. | –N(R¹)(R²) | Aryl (R³,R⁴,R⁵,R⁶) | R⁷ | Melting point/°C |
|---|---|---|---|---|
| 51 | –NH–(2-CH₃, 4-Cl-phenyl) | phenyl | Cl | 220–222 |
| 52 | –NH–CH(CH₃)–C₆H₅ | phenyl | Cl | 138–139 (diastereomer A) |
| 53 | –NH–(2-C₂H₅-phenyl) | phenyl | Cl | 173–175 |
| 54 | –NH–(4-cyclohexyl-phenyl) | phenyl | H | Cl | 245 |
| 55 | –NH–CH(CH₃)–C₆H₅ | phenyl | Cl | 138–139 (diastereomer B) |
| 56 | –NH–CH(CH₃)–(4-OCH₃-C₆H₄) | phenyl | Cl | 55–58 |
| 57 | –NH–CH(CH₃)–(4-Cl-C₆H₄) | phenyl | Cl | 75 (R form) |
| 58 | –NH–CH₂–C₆H₅ | phenyl | Cl | 152–154 |
| 59 | –NH–(2-i-C₃H₇-phenyl) | phenyl | Cl | 172–174 |
| 60 | –NH–(3-CH₃-phenyl) | phenyl | Cl | 168 |

-continued $$\text{(I)}$$

| Ex. No. | —N(R¹)(R²) | R³,R⁴,R⁵,R⁶ (phenyl) | R⁷ | Melting point/°C. |
|---|---|---|---|---|
| 61 | —NH—C₆H₄—NH—CO—CH₃ (para) | phenyl | Cl | 230–232 |
| 62 | —NH—C₆H₄—NO₂ (para) | phenyl | Cl | 261–263 |
| 63 | —NH—C₆H₃(CH₃)₂ (3,4-dimethyl) | phenyl | Cl | 194 |
| 64 | —NH—CH(CH₃)—C₆H₄—CH₃ (ortho) | phenyl | Cl | 137–139 (diastereomer A) |
| 65 | —N(C₂H₅)—C₆H₅ | phenyl | Cl | 135–137 |
| 66 | —NH—C₆H₄—Cl (meta) | phenyl | Cl | 177–179 |
| 67 | —NH—C₆H₄—Cl (ortho) | phenyl | Cl | 192–193 |
| 68 | —NH—C₆H₃(CH₃)₂ (2,4-dimethyl) | phenyl | Cl | 197–199 |
| 69 | —NH—CH(CH₃)—C₆H₄—CH₃ (ortho) | phenyl | Cl | 158 (diastereomer B) |

-continued
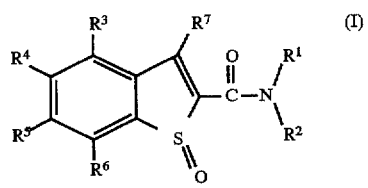
| Ex. No. | -N(R¹)(R²) | R³,R⁴,R⁵,R⁶ (phenyl) | R⁷ | Melting point/°C. |
|---|---|---|---|---|
| 70 | -NH-(2,3-dimethylphenyl) | phenyl | Cl | 192–193 |
| 71 | -NH-(2,5-dimethylphenyl) | phenyl | Cl | 193 |
| 72 | -NH-(2,4,5-trimethylphenyl) | phenyl | Cl | 188–190 |
| 73 | -NH-(3,5-dimethylphenyl) | phenyl | Cl | 209–210 |
| 74 | -NH-(2,4,6-trimethylphenyl) | phenyl | Cl | 172–174 |
| 75 | -NH-CH₂-(4-bromophenyl) | phenyl | Cl | 172 |
| 76 | -NH-(2-methylphenyl) | phenyl | Cl | 188–190 |

-continued
 (I)
| Ex. No. | -N(R¹)(R²) | R³,R⁴,R⁵,R⁶ (phenyl) | R⁷ | Melting point/°C |
|---|---|---|---|---|
| 77 | -NH-(2,6-dimethylphenyl) | o-phenyl | Cl | 198–200 |
| 78 | -N(n-C₄H₉)-C₆H₅ | o-phenyl | Cl | 153 |
| 79 | -NH-CH(CH₃)-(4-chlorophenyl) | o-phenyl | Cl | 60 |
| 80 | -NH-(2,4-dichlorophenyl) | o-phenyl | Cl | 214–216 |
| 81 | -NH-(4-methoxyphenyl) | o-phenyl | Cl | 194 |
| 82 | -NH-CH₂-(4-fluorophenyl) | o-phenyl | Cl | 149–150 |
| 83 | -NH-CH₂-(4-chlorophenyl) | o-phenyl | Cl | 169–171 |
| 84 | -NH-(2-isopropylphenyl) | o-phenyl | H | 176–179 |
| 85 | -NH-(4-cyclohexylphenyl) | o-phenyl | H | 255–256 |

-continued structure (I): Ar-C(R⁷)=C(S(=O))-C(=O)-NR¹R²
where Ar is phenyl substituted with R³, R⁴, R⁵, R⁶

| Ex. No. | —NR¹R² | R³,R⁴,R⁵,R⁶ (aryl) | R⁷ | Melting point/°C |
|---|---|---|---|---|
| 86 | —NH—(2,6-diisopropylphenyl) | phenyl | H | 218–220 |
| 87 | —NH—(4-ethylphenyl) | phenyl | H | 217–218 |
| 88 | —NH—(2-ethylphenyl) | phenyl | H | 158–159 |
| 89 | —NH—(2-methyl-3-chlorophenyl) | phenyl | H | 225–226 |
| 90 | —NH—(2-methyl-5-chlorophenyl) | phenyl | H | 236–237 |
| 91 | —NH—(2-methyl-4-chlorophenyl) | phenyl | H | 199–201 |
| 92 | —NH—(2,3-dichlorophenyl) | phenyl | H | 208–209 |
| 93 | —NH—(4-trifluoromethoxyphenyl) | phenyl | H | 238–240 |

-continued

| Ex. No. | $-N\begin{smallmatrix}R^1\\R^2\end{smallmatrix}$ | $R^3, R^4, R^5, R^6$ ring | $R^7$ | Melting point/°C |
|---|---|---|---|---|
| 94 | 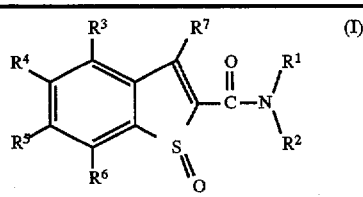 | 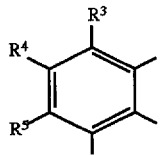 | H | 95–97 |
| 95 | 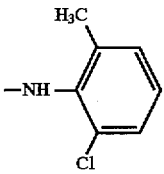 | 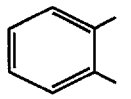 | H | 121–123 |
| 96 | —NH—(CH$_2$)$_2$—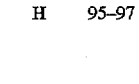 | 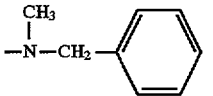 | H | 190–191 |
| 97 | —NH—(CH$_2$)$_6$—CH$_3$ | 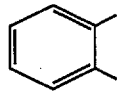 | H | 141 |

Use Examples

In the Use Examples which follow, the compound given below was employed as comparison substance:

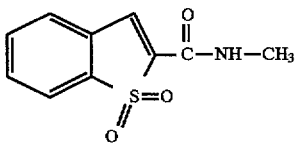 (A)

N-methyl-benzothiophene-2-carboxamide S,S-dioxide (disclosed in DE-OS (German Published Specification) 4 115 184).

Example A

Phytophthora Test (tomato)/protective

Solvent: 4.7 parts by weight of acetone

Emulsifier: 0.3 past by weight of alkyl-aryl polyglycol ether

To produce a suitable preparation of active compound, one part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are then placed in an incubation cabin at 20° C. and a relative atmospheric humidity of about 100%.

The test is evaluated 3 days after inoculation. In this test, a degree of effectiveness of at least 60 % is shown, for example, by the compounds of Preparation Examples 8, 9, 10 and 11 at an active compound concentration in the spray mixture of 10 ppm, while comparison substance (A) shows no activity.

TABLE A

Phytophthora test (tomato)/protective

| Active compound | | Degree of effectiveness in % of the untreated control at an active compound concentration of 10 ppm |
|---|---|---|
| 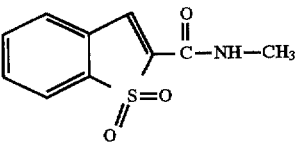 | (A) | 0 |
| (known) 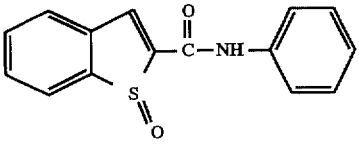 | (8) | 72 |
| 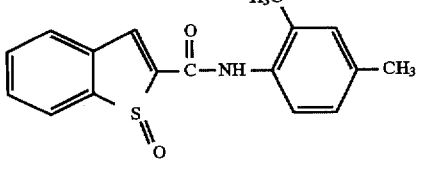 | (9) | 66 |
| 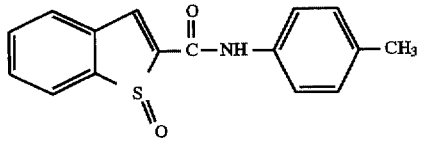 | (10) | 81 |
| 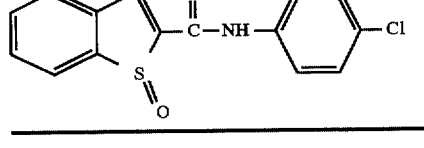 | (11) | 62 |

Example B

Protection of materials test

To detect an antifungal action, the minimum inhibitory concentrations (MIC values) of compounds according to the invention are determined:

An agar prepared using malt extract is treated with active compounds according to the invention in concentrations from 0.1 mg/l to 5,000 mg/l. After the agar has solidified, it is contaminated with pure cultures of *Penicillium brevicaule, Chaetomium globosum* and *Aspergillus niger*. After the agar plate had been stored for two weeks at 28° C. and a relative atmospheric humidity of 60 to 70%, the minimum inhibitory concentration (MIC value) is determined. The MIC value characterizes the lowest concentration of active compound at which no growth whatsoever of the microbe species used is observed on the agar.

In this test, a minimum inhibitory concentration of in some cases less than 50 mg/l is shown, for example, by the compounds of the following preparation examples: 4, 7, 15, 16, 18, 22, 23, 27, 35, 36, 37, 38, 56, 58, 63, 65, 66, 67, 68, 70, 72, 73, 74, 75, 80, 82 and 83.

TABLE B

Protection of materials test

| Active compound | | Minimum inhibitory concentration (MIC value) in mg/l | | |
|---|---|---|---|---|
| | | Penicillium | Chaetomium | Aspergillus |
| benzothiophene-S-oxide-C(O)-NH-n-C$_4$H$_9$ | (4) | <50 | <50 | 200 |
| benzothiophene-S-oxide-C(O)-NH-n-C$_3$H$_7$ | (7) | <50 | 75 | 200 |
| benzothiophene-S-oxide-C(O)-NH-i-C$_4$H$_9$ | (15) | 75 | 75 | 200 |
| benzothiophene-S-oxide-C(O)-NH-t-C$_4$H$_9$ | (16) | 100 | 100 | 300 |
| benzothiophene-S-oxide-C(O)-NH-CH(CH$_3$)-phenyl | (18) | <50 | 100 | 200 |
| benzothiophene-S-oxide-C(O)-NH-C(CH$_3$)$_2$-C$_2$H$_5$ | (22) | 100 | 100 | 200 |
| benzothiophene-S-oxide-C(O)-NH-cyclohexyl | (23) | <50 | <50 | 75 |
| benzothiophene-S-oxide-C(O)-NH-CH(CH$_3$)-(2-CH$_3$-phenyl) | (27) | <50 | 150 | 200 |
| benzothiophene-S-oxide-C(O)-NH-(4-OCH$_3$-phenyl) | (35) | <50 | <50 | <50 |

TABLE B-continued
Protection of materials test
| Active compound | Minimum inhibitory concentration (MIC value) in mg/l | | |
|---|---|---|---|
| | Penicillium | Chaetomium | Aspergillus |
| 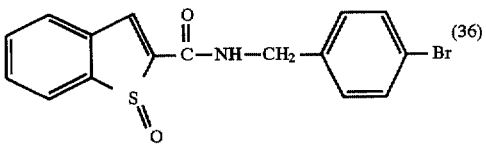 (36) | <50 | 400 | >600 |
| 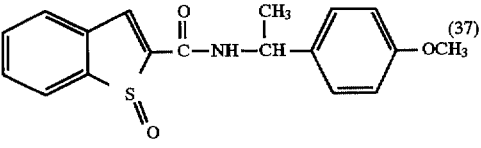 (37) | 75 | 100 | 200 |
| 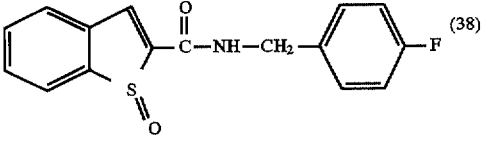 (38) | <50 | <50 | 600 |
| 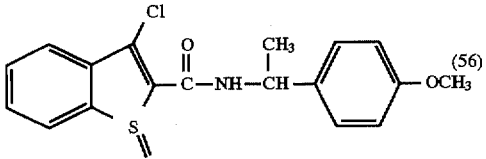 (56) | <50 | <50 | <50 |
| 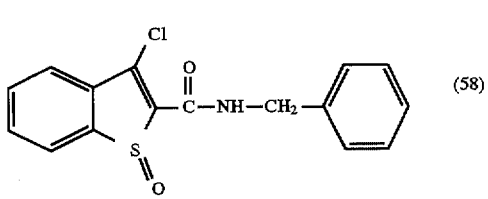 (58) | <50 | <50 | <50 |
| 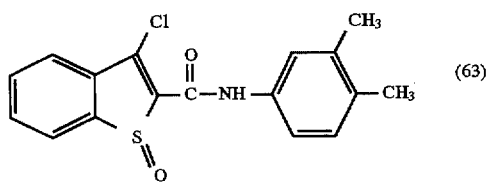 (63) | <50 | <50 | 75 |
| 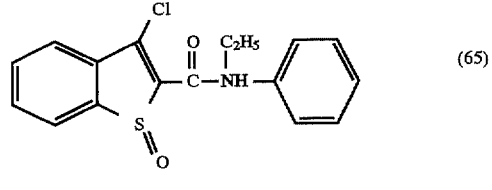 (65) | 200 | 100 | 200 |
| 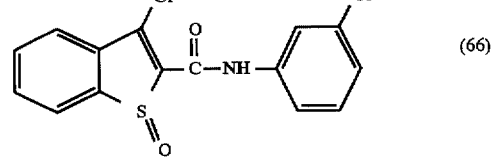 (66) | <50 | <50 | <50 |

TABLE B-continued
Protection of materials test
| Active compound | Minimum inhibitory concentration (MIC value) in mg/l | | |
|---|---|---|---|
| | Penicillium | Chaetomium | Aspergillus |
| 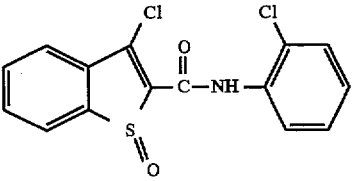 (67) | <50 | <50 | >600 |
| 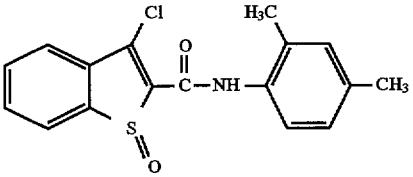 (68) | <50 | <50 | >600 |
| 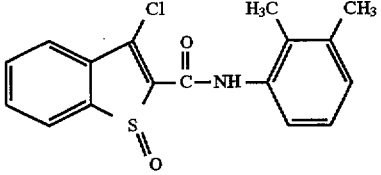 (70) | <50 | <50 | <50 |
| 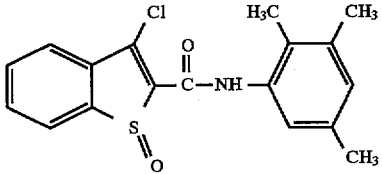 (72) | <50 | <50 | <50 |
| 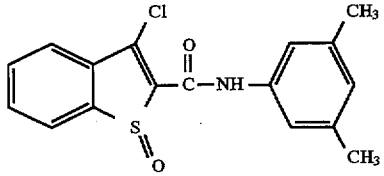 (73) | <50 | <50 | 75 |
| 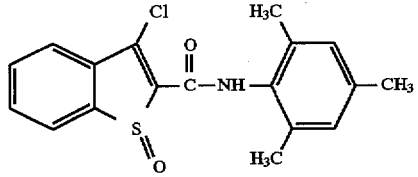 (74) | <50 | <50 | <50 |
| 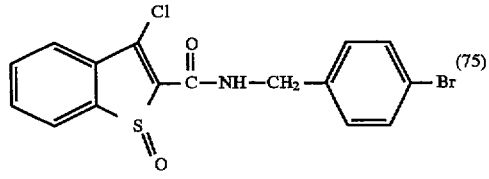 (75) | <50 | <50 | <50 |

TABLE B-continued

Protection of materials test

| Active compound | Minimum inhibitory concentration (MIC value) in mg/l | | |
|---|---|---|---|
| | Penicillium | Chaetomium | Aspergillus |
| (80) | >600 | 600 | >600 |
| (82) | <50 | <50 | <50 |
| (83) | <50 | <50 | <50 |

It must be mentioned that the description and the examples illustrate the present invention, but do not impose any limitation, and that other embodiments in connection with the principle and scope of the invention will be self-evident for those skilled in the art.

We claim:

1. A benzothiophenecarboxamide-S-oxide of the formula

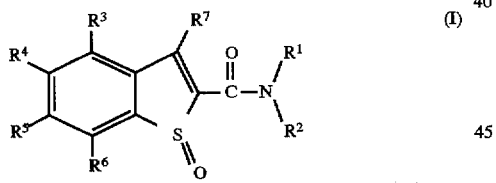

(I)

in which $R^1$ represents straight-chain or branched alkyl having 1 to 18 carbon atoms, or represents cycloalkyl having 3 to 6 carbon atoms, or represents arylalkyl, or aryl, each of which has carbon atoms in the aryl moiety and up to 8 carbon atoms in the straight-chain or branched alkyl, moiety and each of which is optionally mono- to trisubstituted in the aryl moiety by identical or different substituents, selected from the group consisting of halogen, nitro, straight-chain or branched alkyl, or alkoxy each of which has 1 to 4 carbon atoms, cycloalkyl having 3 to 7 carbon atoms, straight-chain or branched halogenoalkoxy which has 1 to 4 carbon atoms and 1 to 9 identical or different halogen atoms, or straight-chain or branched alkylcarbonyl, $R^2$ represents hydrogen or represents straight-chain or branched alkyl having 1 to 4 carbon atoms, $R^3$, $R^4$ $R^5$ and $R^6$ represent hydrogen, and $R^7$ represents hydrogen or chlorine.

2. A benzothiophenecarboxamide S-oxide according to claim 1, in which $R^1$ represents methyl, ethyl, n- or i-propyl, n-, i-, s- or t-butyl, n- or i-pentyl, n- or i-hexyl, n- or i-heptyl, n- or i-octyl, n- or i-nonyl, n- or i-decyl, n- or i-dodecyl, or n- or i-octadecyl, or represents cyclopropyl, cyclopentyl, cyclohexyl, or furthermore, represents phenylalkyl, or phenyl each of which has, up to 6 carbon atoms in the straight-chain or branched alkyl, moiety and each of which is optionally mono- to trisubstituted by identical or different substituents, wherein the aryl substituents are selected from the group consisting of fluorine, chlorine, bromine, nitro, methyl, ethyl, n- or i-propyl, n-, i-, s-or t-butyl, methoxy, ethoxy, n-or i-propoxy, n-, i-, s-or t-butoxy, cyclopropyl, cyclopentyl, cyclohexyl, cycloheptyl, trifluoromethoxy, methylcarbonyl and ethylcarbonyl.

$R^2$ represents hydrogen, methyl, ethyl, n- or i-propyl, n-, i-, s- or t-butyl, n- or i-hexyl, $R^3$, $R^4$, $R^5$ and $R^6$ represent hydrogen and $R^7$ represents hydrogen or chlorine.

3. A microbicidal composition comprising a microbicidally effective amount of a benzothiophenecarboxamide S-oxide according to claim 1 and an inert diluent.

4. A method of combatting undesired microorganisms in plant protection and in the preservation of materials, which method comprises applying to such undesired microorganisms or the their habitat a microbicidally effective amount of a compound according to claim 1.

* * * * *